United States Patent
Ruhge et al.

(10) Patent No.: US 9,726,628 B2
(45) Date of Patent: Aug. 8, 2017

(54) HARDWARE AND METHOD FOR IMPLEMENTATION OF IN SITU ACOUSTIC THERMOGRAPH INSPECTIONS

(71) Applicant: SIEMENS ENERGY, INC., Orlando, FL (US)

(72) Inventors: Forrest R. Ruhge, Orlando, FL (US); Clifford Hatcher, Jr., Orlando, FL (US); James P. Williams, Orlando, FL (US); Joshua DeAscanis, Oviedo, FL (US); Robert G. Shannon, Oviedo, FL (US)

(73) Assignee: SIEMENS ENERGY, INC., Orlando, FL (US)

( * ) Notice: Subject to any disclaimer, the term of this patent is extended or adjusted under 35 U.S.C. 154(b) by 478 days.

(21) Appl. No.: 14/480,733

(22) Filed: Sep. 9, 2014

(65) Prior Publication Data

US 2016/0069829 A1    Mar. 10, 2016

(51) Int. Cl.
*G01N 25/72* (2006.01)
*F01D 25/28* (2006.01)

(52) U.S. Cl.
CPC ............ *G01N 25/72* (2013.01); *F01D 25/285* (2013.01); *F05D 2260/83* (2013.01); *F05D 2270/80* (2013.01)

(58) Field of Classification Search
None
See application file for complete search history.

(56) References Cited

U.S. PATENT DOCUMENTS

| | | | |
|---|---|---|---|
| 6,399,948 B1 | 6/2002 | Thomas et al. | |
| 7,689,465 B1* | 3/2010 | Shakes | G06Q 10/08 705/27.1 |
| 2004/0057492 A1* | 3/2004 | Vona | G01N 25/72 374/45 |
| 2007/0163352 A1* | 7/2007 | Nielsen | B61K 9/10 73/668 |
| 2008/0250860 A1* | 10/2008 | Clossen-von Lanken Schulz .... | G01N 29/11 73/627 |
| 2011/0169961 A1* | 7/2011 | Wu | G01J 5/02 348/164 |
| 2012/0136630 A1* | 5/2012 | Murphy | G05D 1/0094 702/188 |

* cited by examiner

*Primary Examiner* — Erica Lin

(57) ABSTRACT

A system and method include an acoustic thermography stack and a frame that the stack is slidably mounted to. The frame includes an end frame portion with a blade stop, and an air cylinder provides force to move the stack up and down a rail of the frame such that a turbine blade may be clamped between a cap of the stack and the blade stop. The clamped blade is excited using the stack, and an infrared camera is used to detect critical indications in the blade.

7 Claims, 7 Drawing Sheets

HARDWARE AND METHOD FOR IMPLEMENTATION OF IN SITU ACOUSTIC THERMOGRAPH INSPECTIONS

BACKGROUND OF THE INVENTION

Field of the Invention

This invention relates generally to a system and method for performing thermograph inspection of turbine blades and, more particularly, to a system and method for performing acoustic thermograph inspection of turbine blades without removing the blades from the turbine so as to eliminate the need for costly blade removal to perform the inspection.

Discussion of the Related Art

The world's energy needs continue to rise which provides a demand for reliable, affordable, efficient and environmentally-compatible power generation. A turbine engine is one known machine that provides efficient power, and often has application for an electric generator in a power plant, or engines in an aircraft or a ship. A typical gas turbine engine includes a compressor section, a combustion section and a turbine section. The compressor section provides a compressed air flow to the combustion section where the air is mixed with a fuel, such as natural gas, and ignited to create a hot working gas. The working gas expands through the turbine section and is directed across rows of blades therein by associated vanes. As the working gas passes through the turbine section, it causes the blades to rotate, which in turn causes a shaft to rotate, thereby providing mechanical work.

Maintaining the structural integrity of the blades in a turbine is important for proper operation of the turbine. Thus, it is very important to periodically check the blades for signs of deterioration, such as cracks and defects. One known technique for testing for material defects in the blades includes treating the blades with a dye penetrant so that the dye enters any crack or defect that may be present. The blades are then cleaned, and the structure is treated with a powder that causes the dye remaining in the cracks to wick into the powder. An ultraviolet (UV) light source is used to inspect the material to observe locations on the component that fluoresces as a result of the dye. This technique is disadvantageous, however, because it is inspector intensive and dependent and requires the person to be skilled. Additionally, the dye does not typically penetrate tightly closed cracks or cracks that are not on the surface.

A second known technique for inspecting a component for defects employs an electromagnetic coil to induce eddy currents in the blade. The coil is moved around on the blade, and the eddy current pattern changes at a crack or other defect. When the eddy current pattern changes a complex impedance in the coil changes, which can be observed on an oscilloscope. This technique has the drawback that it is also very operator intensive, slow and tedious.

A third known technique employs thermal imaging of the component to identify the defects. Typically, a heat source, such as a flash lamp or a heat gun, is used to direct a planar pulse of heat to the surface of the component. The material of the component absorbs the heat, and emits reflections in the infrared wavelengths. Certain types of defects will cause the surface temperature to cool at a different rate over the defects than for the surrounding areas. A thermal or infrared imaging camera is used to image the component and detect the resulting surface temperature variation. Although this technique has been successful for detecting disbands and corrosion, it is ordinarily not successful at detecting vertical cracks in the material, i.e., those cracks that are perpendicular to the surface. This is because a fatigue crack looks like a knife edge to the planar heat pulse, and therefore no, or minimal, reflections occur from the crack, making the cracks difficult or impossible to see in the thermal image.

Thermal imaging for detecting defects in a material that is capable of detecting small cracks as well as tightly closed cracks is described in U.S. Pat. No. 6,399,948 issued to Thomas et al. on Jun. 4, 2002. However, this technique requires the material that is being inspected to be placed in a thermal imaging system. Thus, if the material to be inspected includes turbine blades, the blades must be removed from the turbine to be inspected. Removal of turbine blades is costly, time-consuming and labor intensive. Thus, there is a need in the art for a system and method that allows for thermal imaging of turbine blades without removing the blades from the turbine.

SUMMARY OF THE INVENTION

This disclosure describes a system and method for performing acoustic thermography inspection of turbine blades. The system and method include an acoustic thermography stack and a frame that the stack is slidably mounted to. The frame includes an end frame portion with a blade stop, and an air cylinder provides force to move the stack up and down a rail of the frame such that a turbine blade may be clamped between a cap of the stack and the blade stop. The clamped blade is excited using the stack, and an infrared camera is used to detect critical indications in the blade.

Additional features of the present invention will become apparent from the following description and appended claims, taken in conjunction with the accompanying drawings.

DETAILED DESCRIPTION OF THE EMBODIMENTS

The following discussion of the embodiments of the invention directed to a system and method for performing in situ acoustic thermograph inspection is merely exemplary in nature, and is in no way intended to limit the invention or its applications or uses. For example, while in situ thermograph inspection of turbine blades in a steam turbine are described herein, other types of in situ acoustic thermograph inspection may be used according to the system and method of the present invention.

Figure 1:
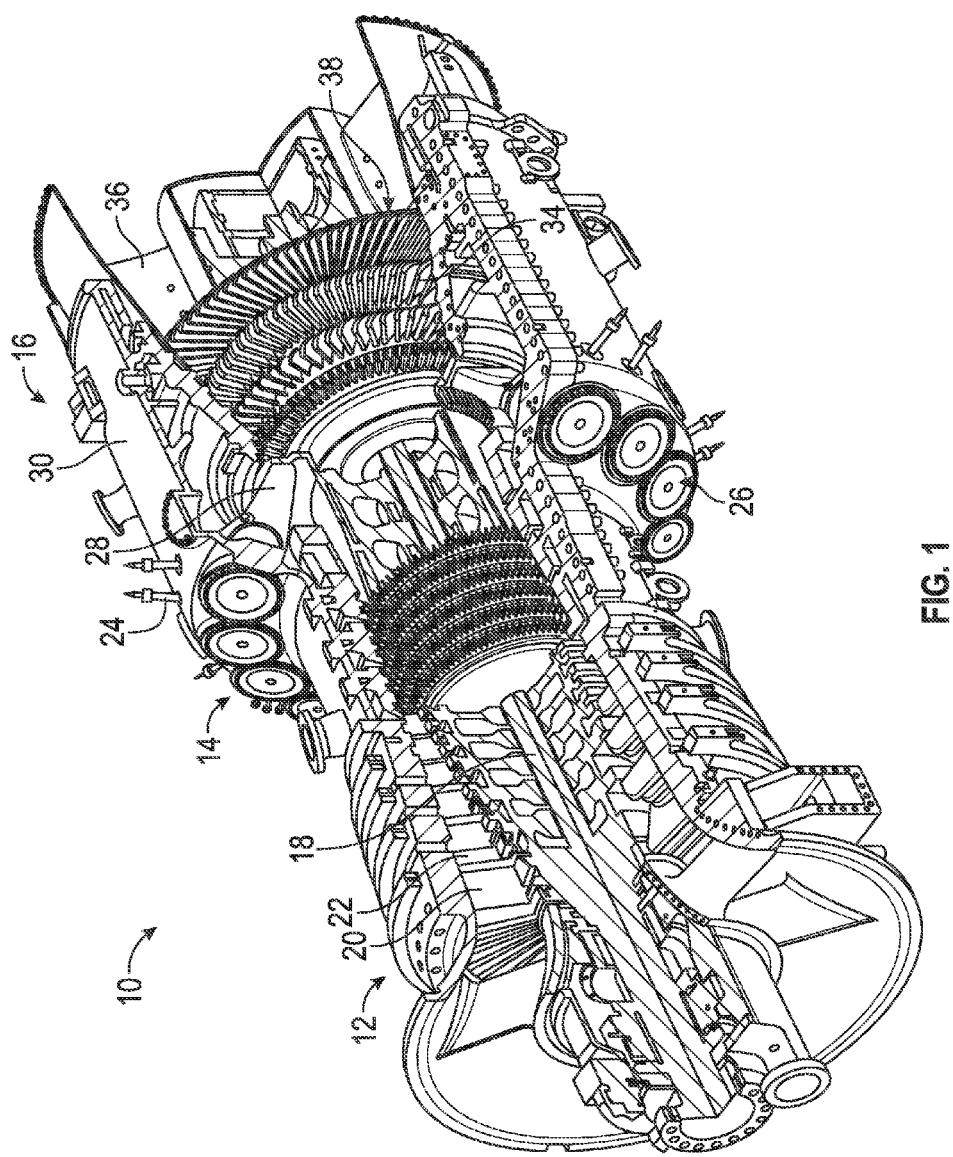
FIG. 1 is an illustration of a gas turbine engine.

FIG. 1 is a cut-away, isometric view of a gas turbine engine 10 including a compressor section 12, a combustion section 14 and a turbine section 16 all enclosed within an outer housing 30, where operation of the engine 10 causes a central shaft or rotor 18 to rotate, thus creating mechanical work. The engine 10 is illustrated and described by way of a non-limiting example to give context to the invention discussed below. Those skilled in the art will appreciate that other gas turbine engine designs will also benefit from the invention. Rotation of the rotor 18 draws air into the compressor section 12 where it is directed by vanes 22 and compressed by rotating blades 20 to be delivered to the combustion section 14 where the compressed air is mixed with a fuel, such as natural gas, and where the fuel/air mixture is ignited to create a hot working gas. More specifically, the combustion section 14 includes a number of circumferentially disposed combustors 26 each receiving the fuel that is injected into the combustor 26 by an injector (not shown) and mixed with the compressed air to be ignited by an igniter 24 to create the working gas, which is directed by a transition 28 into the turbine section 16. The working gas is directed by circumferentially disposed stationary vanes (not shown) in the turbine section 16 to flow across circumferentially disposed rotatable turbine blades 34, which causes the turbine blades 34 to rotate, thus rotating the rotor 18. Once the working gas passes through the turbine section 16 it is output from the engine 10 as an exhaust gas through an output nozzle 36.

Each group of the circumferentially disposed stationary vanes defines a row of the vanes and each group of the circumferentially disposed blades 34 defines a row 38 of the blades 34. In this non-limiting embodiment, the turbine section 16 includes four rows 38 of the rotating blades 34 and four rows of the stationary vanes in an alternating sequence. In other gas turbine engine designs, the turbine section 16 may include more or less rows of the turbine blades 34. It is noted that the most forward row of the turbine blades 34, referred to as the row 1 blades, and the vanes, referred to as the row 1 vanes, receive the highest temperature of the working gas, where the temperature of the working gas decreases as it flows through the turbine section 16.

Figure 2:
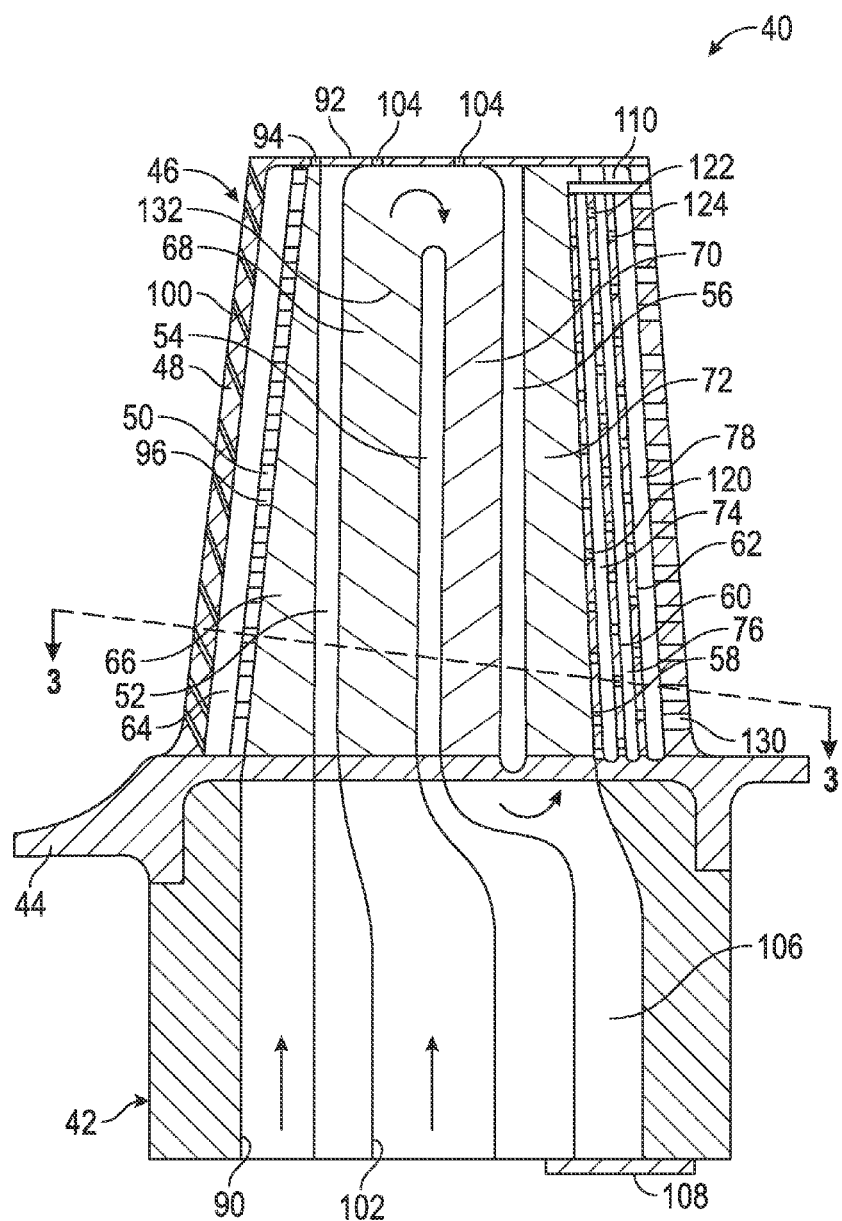
FIG. 2 is an illustration of a known turbine blade separated from a gas turbine engine.
Figure 3:
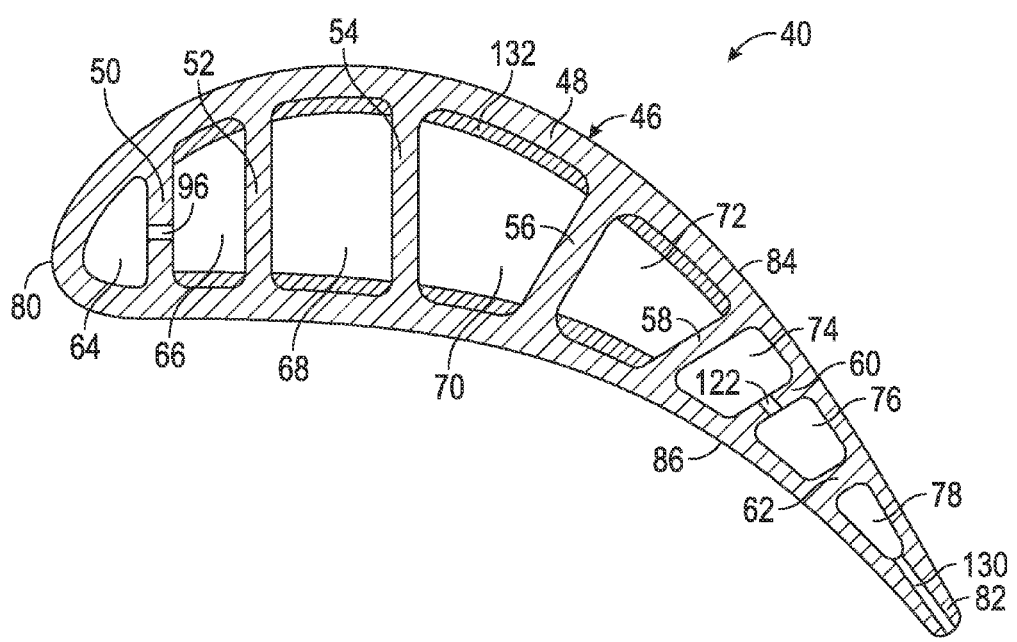
FIG. 3 is an illustration of a cross-sectional view along line 3-3 of the blade shown in FIG. 2.

FIG. 2 is a cross-sectional view of a known airfoil or blade 40 that is intended to represent a row 1 blade, but can be a general representation of any of the blades 34 in the rows in the gas turbine engine 10, where the blade 40 includes cooling airflow channels discussed in detail below. FIG. 3 is a cross-sectional view of the blade 40 along line 3-3 in FIG. 2. The blade 40 includes an attachment portion 42 that is configured to allow the blade 40 to be securely mounted to the rotor 18 in a manner well understood by those skilled in the art. A blade platform 44 is provided at a distal end of the attachment portion 42 and defines the beginning of a tapered airfoil portion 46 of the blade 40. The airfoil portion 46 includes a pressure side (P/S) 86 and a suction side (S/S) 84 defined by the pressure present on the airfoil portion 46 as it rotates. Further, the airfoil portion 46 also includes a leading edge 80 and a trailing edge 82.

The airfoil portion 46 includes an outer housing 48 and a number of internal ribs 50, 52, 54, 56, 58 60 and 62, typically configured as a single piece insert and being made of ceramic, that define a series of flow channels. The flow channels include a shower head flow channel 64 between the outer housing 48 and the rib 50, a flow channel 66 between the rib 50 and the rib 52, a flow channel 68 between the rib 52 and the rib 54, a flow channel 70 between the rib 54 and the rib 56, a flow channel 72 between the rib 56 and the rib 58, an impingement flow channel 74 between the rib 58 and the rib 60, an impingement flow channel 76 between the rib 60 and the rib 62, and an impingement flow channel 78 between the rib 62 and the outer housing 48. The flow channels 68, 70 and 72 combine to make up a serpentine flow channel. Air flows into the blade 40 through an input opening 90 in the attachment portion 42, enters the channel 66 and flows towards an end portion 92 of the housing 48, where some of the airflow exits the flow channel 66 through orifices 94. Some of that air flows through orifices 96 in the rib 50 into the shower head channel 64 and out of the airfoil portion 46 through a series of orifices 100 that are angled upward towards the end portion 92. Airflow also enters the blade 40 through an opening 102 in the attachment portion 42 and flows into the channel 68 where some of the airflow flows out orifices 104. Most of the airflow flows into the channel 70 to flow back down the airfoil 46 and into a chamber 106 in the attachment portion 42 that has an opening covered by a cover plate 108. The air then flows back up the blade 40 through the channel 72 and through orifices 110 in the housing 48.

The rib 58 includes a series of orifices 120 that allow the air to flow into the channel 60 between the ribs 58 and 60, the rib 60 includes a series of orifices 122 that allow the air to flow into the channel 62 between the ribs 60 and 62, and the rib 62 includes a series of orifices 124 that allow the air to flow into a channel 94 between the rib 58 and the outer housing 48. A series of orifices 130 in the outer housing 48 allows the air to flow out of the blade 40. As is apparent, the orifices 120, 122 and 124 in the ribs 58, 60 and 62 are staggered relative to each other so that the air does not flow directly from one channel across the next channel into the following channel. This causes the air flowing through one of the orifices to strike a section of the rib in the next channel also creating turbulence that increases the cooling effect. Particularly, this airflow effect creates vortexes inside of the channels 74, 76 and 78 that also provide turbulence for effective cooling.

It is known in the art to provide a configuration of turbulators or trip strips mounted to the inner walls of the flow channel portions 66, 68, 70 and 72, represented generally as reference number 132 in FIG. 2. A trip strip for this purpose is typically a metal strip formed to an inside surface of the outer housing 48 of the blade 40 in a transverse direction to the flow of the cooling air. In this design, the trip strips 132 are shown as skewed trip strips in that they are angled slightly relative to the direction of the flow of the cooling air. In an alternate embodiment, the trip strips 132 can be normal to the flow direction of the air. Skewed trip strips are sometimes employed over normal trip strips so as to allow the trip strip to be longer, which provides more turbulent airflow.

Because of the temperature and air vortexes experienced by the blades 34, the blades 34 need to be periodically inspected. Particularly, it is known that the trailing edge 82 of the blade 34 is known to exhibit erosion with use over time. Indications in the eroded region are difficult to detect using the traditional inspection techniques such as liquid penetrant and ultrasonic or eddy current inspection methods. For example, during liquid penetrant inspections, the penetrant is used to detect indications as they grow large enough to be detected outside of the erosion region. Erosion traps penetrant which bleeds out during the development process, thereby obscuring relevant indications. Thus, if the erosion region extends far enough into the blade, the indications must reach a critical size before they can be regarded as a crack. In other words, this method give false indications causing blades to be pulled from the turbine when it may not be necessary to do so. Additionally, the surface roughness from the erosion causes inadequate coupling or large background noise when using ultrasonic or eddy current inspection methods making relevant indication determinations difficult.

Acoustic thermography can detect small indications that exist only in the erosion region without suffering the negative effect of the noise related to the erosion, as described in the '948 patent issued to Thomas et al. and discussed above. While this method has been applied in the field with success, it requires the removal of the turbine blades from the steam turbine unit. Removal of the blades for inspection is both costly and time-consuming, as stated above.

Figure 4:
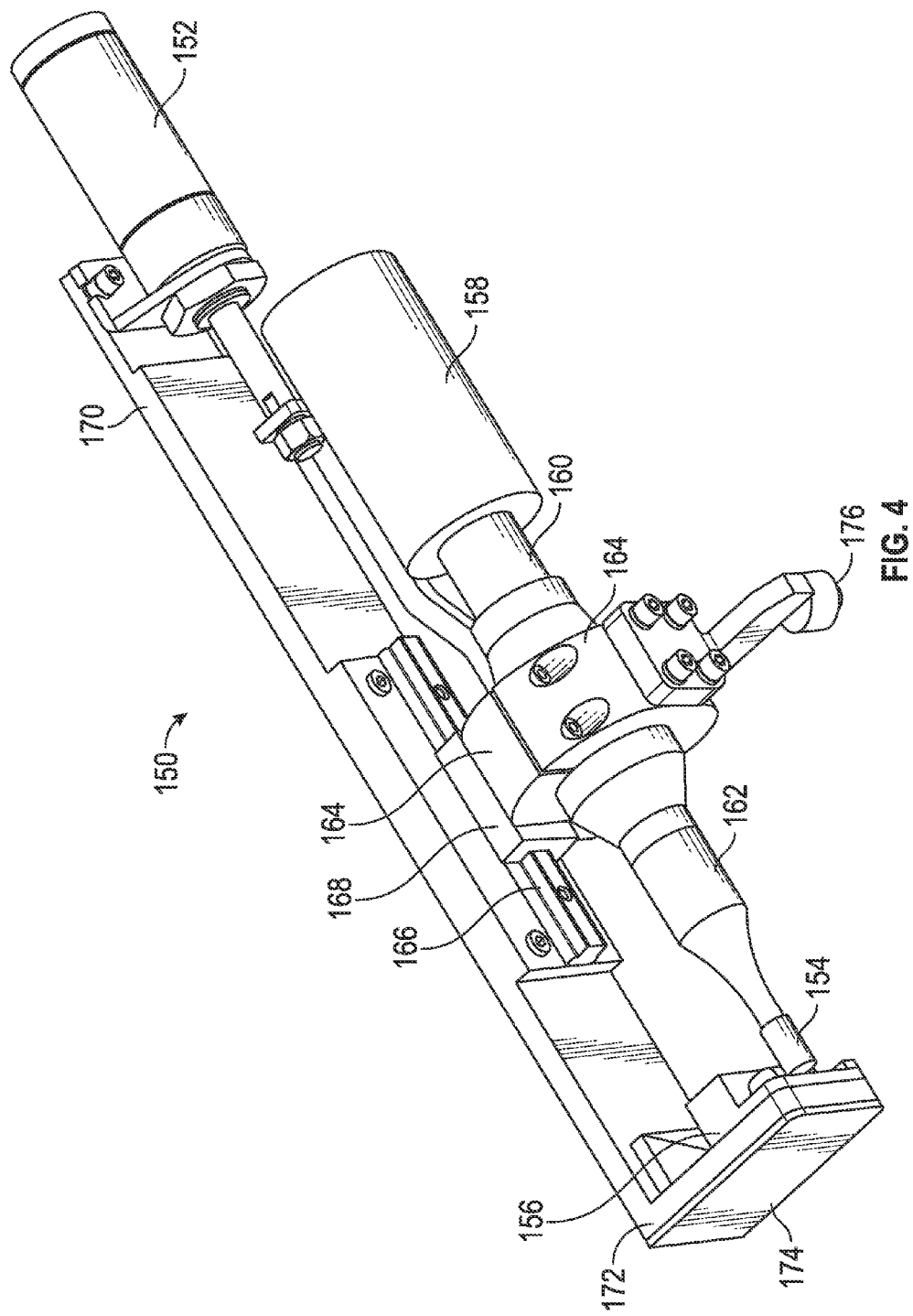
FIG. 4 is an illustration of an embodiment of a system for performing acoustic thermography of turbine blades that are part of an assembled steam turbine.

FIG. 4 is an illustration of an embodiment of a system 150 that is capable of performing in situ acoustic thermography of turbine blades in an assembled steam turbine, where the system 150 is capable of detecting critical indications in the turbine blades before they extend beyond the erosion region. An air cylinder 152 is used to control a clamping and unclamping function that forces a cap 154 to press against a blade inserted between the cap 154 and a blade stop 156 as described in more detail below. The blade stop 156 is attached to an end frame portion 172. Opposite to the blade stop 156 on the end frame portion 172 may be a protective bottom plate 174 that protects the blades being inspected from damage from the end frame portion 172. This is necessary because the blade that is being inspected is clamped at a trailing edge region and not at a blade root region as is done according to known methods in the art. Any suitable material, such as plastic, may be used for the protective bottom plate 174. The blade stop 156 may be any suitable material, including plastic. The cap 154 serves to dampen the signal to protect a blade that is inserted between the cap 154 and the blade stop 156 from being damaged. The cap 154 is preferably made from brass. Copper, or a mixture that includes copper and brass may be used for the cap 154. The cap 154 is on an end portion of an acoustic thermography stack that is opposite to a horn 158 that is typically made of titanium or a similar material. The cap 154 also serves to protect the horn 158 from becoming brittle and sustaining damage from use. The horn 158 is connected to a piezoelectric portion 160 that is connected to a booster 162 that amplifies the energy of the horn 158 such that a blade that is clamped inserted between the cap 154 and the blade stop 156 is excited using the energy of the horn 158 in a manner known to those skilled in the art. The booster 162 may be any suitable material, including carbon steel. The horn 158, the piezoelectric portion 160, the booster 162 and the cap 154 make up the acoustic thermography stack.

An aluminum bracket 164 clam-shells around the piezoelectric portion 160 and is connected to a block 168 that is slidably moveable along a track 166 of a frame 170. Air pressure from the air cylinder 152 moves the clamp 164 that holds the horn 158, piezoelectric portion 160, booster 162, and cap 154 (i.e., the stack) up and down the track 166 to clamp and unclamp a blade as discussed in detail below. A stack support 176 is attached to the clamp 164 and is used to provide stabilizing support to the piezoelectric portion 160 of the stack.

Figure 5:
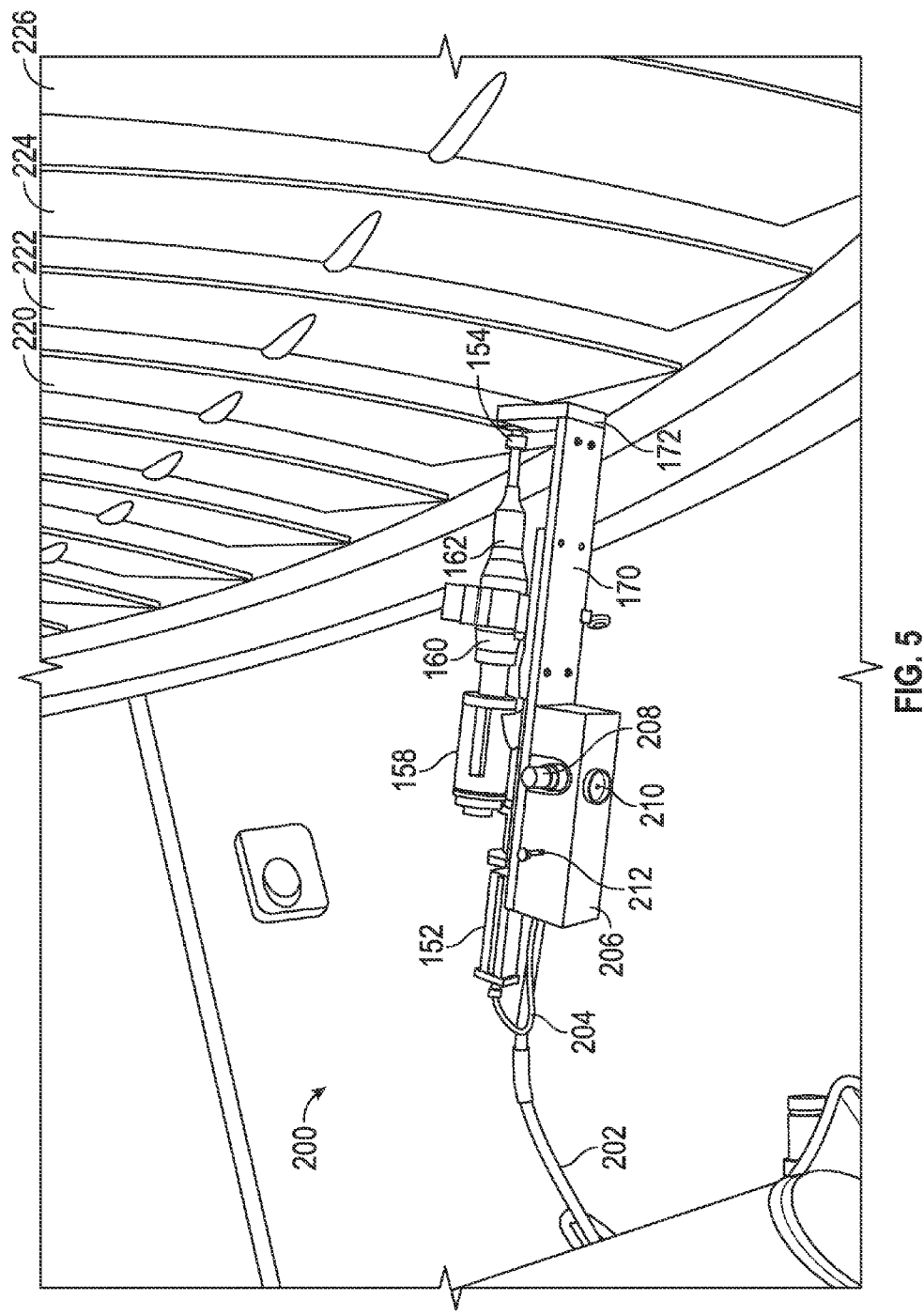
FIG. 5 is an illustration of the system for performing acoustic thermography where the system is being used inside of an assembled steam turbine.

FIG. 5 is an illustration of an embodiment of a system 200 for performing acoustic thermography of turbine blades in an assembled steam turbine, where like elements are identified by the same reference numerals used in FIG. 4. The system 200 is brought inside the turbine through an access door (not shown) so that assembled blades in the turbine may be inspected. An air hose 202 provides air to the system 200, and an air hose 204 provides air to the air cylinder 152 upon actuation. Actuation may occur, for example, via an actuating switch 212. However, any suitable method and/or mechanism for actuation may be used. A pressure regulator 208 and a pressure gauge 210 may be used to adjust pressure to the air cylinder 152 in a manner known to those skilled in the art. The air pressure used may vary to provide a desired clamping force. For example, the pressure used to clamp a blade may be 35 psi.

Using the air cylinder 152 to move the stack up and down as described above, a blade 220 is clamped between the cap 154 and the blade stop 156. Once the blade 220 is clamped into place, the blade 220 is excited and inspected as described above. Next, the blade 220 is unclamped and the system 200 is moved such that a blade 222 may be clamped and inspected. This process is repeated such that blades 224 and 226 are inspected. After the blades that are accessible are inspected, for example the blades 220-226, the rotor that the blades are mounted to is turned such that a next set of blades may be inspected. This process is repeated so that all of the blades may be inspected in situ.

Figure 6:
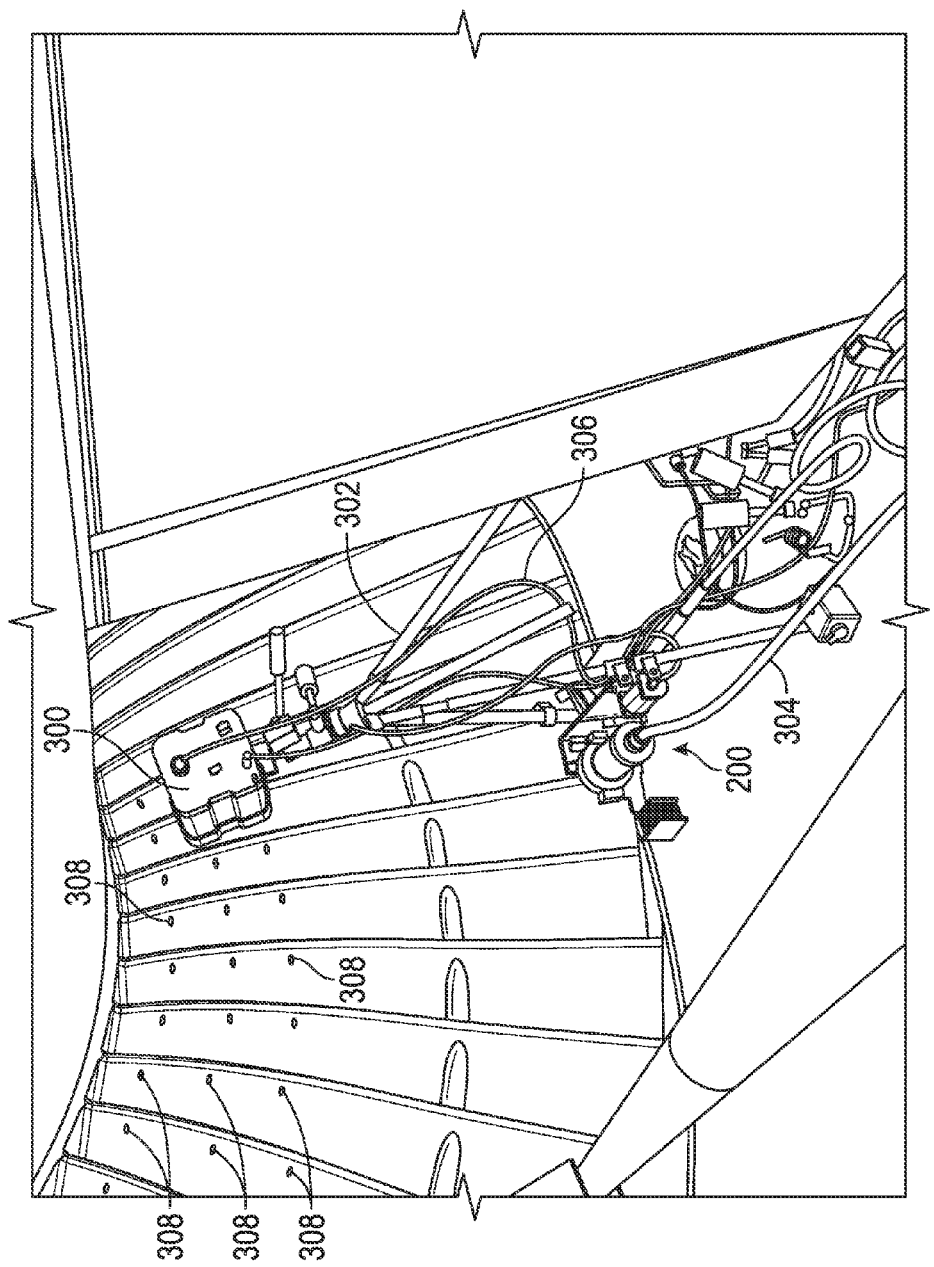
FIG. 6 is an illustration of an infrared camera that is being used with the system according to one embodiment.

FIG. 6 is an illustration of an infrared camera 300 that is being used with the system 200 according to one embodiment of the invention. The camera 300 is mounted on a tripod 302 such that the camera 300 may capture a blade that is being excited by the system 200. A plug 304 provides electrical power to the system 200, and a cable 306 plugs into a computer or computing device via, for example, a USB port. In this way, the system 200 is able to excite a desired blade, and the infrared camera 300 is able to capture images of the excited blade and provide the images to a computer such that a proper analysis/inspection of the blade may be performed. The computer may be a laptop that is brought inside the turbine, or the computer may be external and connected via a long cable or by using a USB/Ethernet converter in a manner known to those skilled in the art. The system 200 may also be controlled remotely using a computer with the appropriate software, or may be mechanically operated by a technician. One or more indicator stickers 308 are placed on the blades to be inspected and are used as signal indicators to verify excitation of a blade has occurs during analysis to confirm that a blade is excited enough to detect a crack or damage in the blade. Thus, if the blade being inspected is not damaged, the camera 300 will not indicate anything in the blade. The indicator sticks 308 will be the only indication that the blade has been excited enough to adequately inspect. If the indicator stickers 308 do not light up in the camera images, it may be determined that the blade being inspected was not excited enough to provide adequate inspection.

Figure 7:
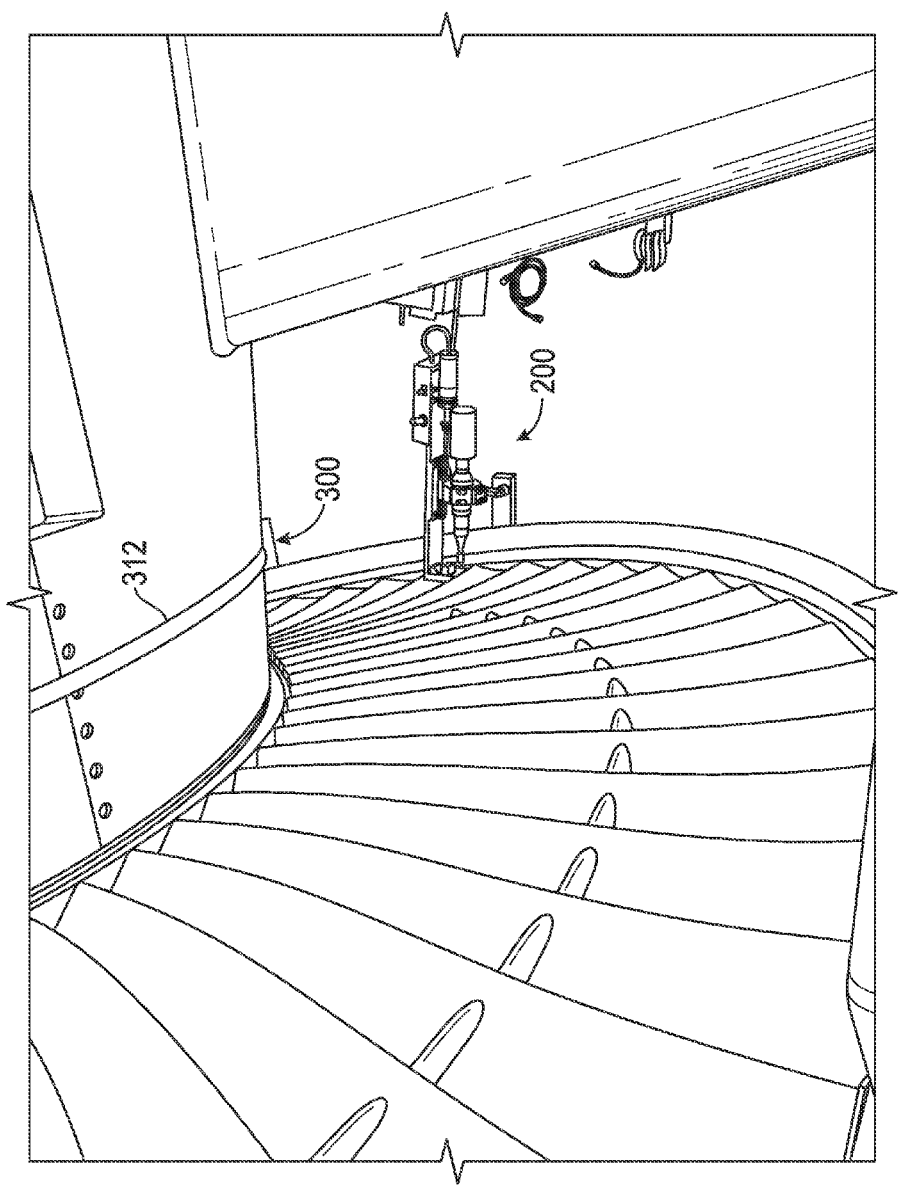
FIG. 7 is an illustration of the infrared camera being used with the system according to another embodiment.

FIG. 7 is an illustration of the infrared camera 300 being used with the system 200 according to another embodiment. In this embodiment, the camera 300 is mounted to a strap 312 and positioned to capture a blade being excited by the system 200. The camera 300 may be adjusted such that it is in a desired position along the strap 312. The strap 312 may be any suitable strap, such as a ratchet strap. The strap 312 extends all the way around a cylinder 310 of the turbine. Although not shown, brackets or any suitable mechanism may be used to attach the camera 300 to the strap 312.

The foregoing discussion discloses and describes merely exemplary embodiments of the present invention. One skilled in the art will readily recognize from such discussion, and from the accompanying drawings and claims, that various changes, modifications and variations can be made therein without departing from the scope of the invention as defined in the following claims.

What is claimed is:

1. A system for performing acoustic thermography inspection of turbine blades while the turbine blades are in place in an assembled turbine, said system comprising:
    an acoustic thermography stack that includes a horn, a piezoelectric portion, a booster and a cap;
    a frame that the acoustic thermography stack is slidably mounted to said frame including an end frame portion with a blade stop;
    an air cylinder that provides force to move the acoustic thermography stack up and down a rail of the frame such that a turbine blade may be clamped between the cap and the blade stop and then excited using the acoustic thermography stack; and
    an infrared camera, said infrared camera being used to detect critical indications in the turbine blade that is clamped between the cap and the blade stop and then excited,
    wherein the cap is made of brass, copper, or a mixture that includes copper and brass.

2. The system according to claim 1 further comprising a clam-shell clamp that clamps the piezoelectric portion of the acoustic thermography stack to a rail of the frame.

3. The system according to claim 1 further comprising a bottom plate of the end frame that protects turbine blades from being damaged.

4. The system according to claim 1 wherein the blade stop is made of plastic.

5. The system according to claim 1 wherein the infrared camera is seated on a tripod.

6. The system according to claim 1 wherein a trailing edge region of the blade is clamped between the cap and the blade stop.

7. The system according to claim 1 further comprising one or more indicator stickers placed on each of the blades to be inspected, said indicator stickers indicating when the turbine blade being inspected has been excited enough to provide a proper inspection, wherein the indicator stickers indicate when the turbine blade being inspected has been excited enough to provide a proper inspection by lighting up in a camera image.

* * * * *